United States Patent
Tanaka et al.

(10) Patent No.: US 6,969,750 B2
(45) Date of Patent: Nov. 29, 2005

(54) WATER ABSORBENT MATERIAL AND ABSORBENT ARTICLE USING SAME

(75) Inventors: Hisakazu Tanaka, Osaka (JP); Toshiya Kato, Osaka (JP); Shigeki Ideguchi, Osaka (JP); Hideyuki Ishizu, Osaka (JP); Yoshiki Hasegawa, Hyogo-ken (JP)

(73) Assignee: Dainippon Ink and Chemicals, Inc., Tokyo (JP)

(*) Notice: Subject to any disclaimer, the term of this patent is extended or adjusted under 35 U.S.C. 154(b) by 107 days.

(21) Appl. No.: 10/088,107

(22) PCT Filed: Jul. 26, 2001

(86) PCT No.: PCT/JP01/06428

§ 371 (c)(1),
(2), (4) Date: Mar. 22, 2002

(87) PCT Pub. No.: WO02/10239

PCT Pub. Date: Feb. 7, 2002

(65) Prior Publication Data

US 2003/0045198 A1 Mar. 6, 2003

(30) Foreign Application Priority Data

Jul. 28, 2000 (JP) .................................... 2000-228767
Mar. 28, 2001 (JP) ...................................... 2001-92573

(51) Int. Cl.[7] .............................................. C08F 26/06
(52) U.S. Cl. ..................... 526/262; 526/258; 526/263; 526/271; 526/303.1; 526/307.2; 526/307.7; 526/317.1; 526/319
(58) Field of Search ............................... 526/262, 258, 526/263, 271, 303.1, 307.2, 307.7, 317.1, 319, 307.1; 510/266, 335, 402

(56) References Cited

U.S. PATENT DOCUMENTS

| 5,531,934 A | * | 7/1996 | Freeman et al. ............ 252/390 |
| 5,633,290 A | * | 5/1997 | Frechet et al. ................ 521/74 |
| 5,658,464 A | * | 8/1997 | Hann et al. .................. 210/697 |
| 5,723,344 A | * | 3/1998 | Mabilat et al. ............. 436/518 |
| 5,756,447 A | | 5/1998 | Hall |

FOREIGN PATENT DOCUMENTS

| JP | 62-27408 | 2/1987 |
| JP | 3-93815 | 4/1991 |
| JP | 7-310021 | 11/1995 |
| JP | 9-143210 | 6/1997 |
| JP | 10-81714 | 3/1998 |
| JP | 10-298282 | 11/1998 |
| JP | 11-60729 | 3/1999 |
| JP | 11-158266 | 6/1999 |
| JP | 2000-63511 | 2/2000 |
| JP | 2000-281915 | 10/2000 |
| JP | 2000-290370 | 10/2000 |

\* cited by examiner

*Primary Examiner*—Tatyana Zalukaeva
(74) *Attorney, Agent, or Firm*—Armstrong, Kratz, Quintos, Hanson, & Brooks, LLP

(57) ABSTRACT

The water absorbent material of the present invention is composed of a copolymer of an anhydropolyamino acid having at least one ethylenically unsaturated double bond in a molecule, a water-soluble monomer having an ethylenically unsaturated double bond and polysaccharides, and has high water absorption ratio and high water absorption rate in pure water or water having a low ion content and also has high absorption properties for high concentration salt-containing solutions.

11 Claims, No Drawings

WATER ABSORBENT MATERIAL AND ABSORBENT ARTICLE USING SAME

TECHNICAL FIELD

The present invention relates to a novel and useful water absorbent material and an absorbent article which utilizes such a material. In particular, the present invention relates to a water absorbent material and an absorbent article for use in the absorption of solutions containing a high concentration of salts, such as sea water, calcium chloride deliquescent solutions, blood, and other body fluids (such as urine and sweat).

A water absorbent material of the present invention can be widely used in fields such as sanitary products and household articles such as disposable diapers, pads, and sanitary napkins, water sealing materials, soil conditioners, anticondensation coatings, water-storing materials for use in agriculture and horticulture, and water swelling rubbers.

BACKGROUND ART

Conventional water absorbent materials include hydrolysates of graft polymers of starch and acrylonitrile, and partially neutralized products of crosslinked polyacrylic acid. Furthermore, examples of water absorbent polyamino acid based resins obtained by hydrolyzing a partially crosslinked product of polyamine polyaspartate have also been disclosed in Japanese Unexamined Patent Application, First Publication, No. Hei 7-309943 and Japanese Unexamined Patent Application, First Publication, No. Hei 9-169840. However, water absorbent materials produced from polyamino acid based resins display insufficient gel strength. Furthermore, although water absorbent materials produced from acrylic resins are typically capable of absorbing between several hundred and several thousand times their own weight of fresh water, this water absorbing ability decreases to an extremely low level for water which contains salts. As a result, in the water absorbent material development field, various trials for enhancing the water absorption capability for water containing salts have been made.

As the water absorbent material having an enhanced water absorption capability for water containing salts, for example, the following suggestions have been made wherein an ionic water absorbent material having a small salt resistance is used in combination with a nonionic water absorbent material having a large salt resistance.

(1) A water swelling polymer comprising a copolymer of an ethylenically unsaturated monomer with a carboxyl group and a base thereof, and a polyoxyalkylene glycol allyl ether with a hydrophobic group at one terminal (Japanese Unexamined Patent Application, First Publication, No. Sho 62-27408); and (2) a water absorbent polymer comprising a copolymer of an ethylene based unsaturated monomer with a carboxyl group and an associated base, and an alkylpolyoxyalkylene glycol mono(meth)acrylate with an alkyl group at one terminal (Japanese Unexamined Patent Application, First Publication, No. Hei 3-93815).

However, in the conventional water absorbent materials described above, although the important characteristics such as the water absorption capability (volume of water absorption, speed of water absorption) and the salt tolerance are improved to some extent, the improvement is not always sufficient.

Furthermore, in order to solve the problems described above, water absorbent materials comprising a copolymer of either a sulfoalkyl (meth)acrylate or an acrylamide (Japanese Unexamined Patent Application, First Publication, No. Hei 10-81714) or a copolymer of a nonionic monomer and acrylic acid (Japanese Unexamined Patent Application, First Publication, No. Hei 9-143210) have also been proposed. However, although these water absorbent materials offer an improved water absorption of water which contains salts, the water absorption for pure water or water with only small amounts of ions actually decreases, and the initial water absorption speed is also slow.

In addition, as an example of a water absorbent material comprising a combination of a polyamino acid and a copolymer comprising a polyacrylic acid, the water absorbing agent composition comprising a polyamino acid and a crosslinked polyacrylate polymer as the main constituents is disclosed in Japanese Unexamined Patent Application, First Publication, No. Hei 7-310021. However, this water absorbent material exhibits little water absorption capability, and even when the surface of the water absorbent resin is crosslinked using a surface crosslinking agent, the gel strength displays no improvement.

An object of the present invention is to provide a water absorbent material which displays superior water absorption of solutions with high concentrations of salts such as sea water, calcium chloride deliquescent solutions, blood, and other body fluids (such as urine and sweat) and further suffers no deterioration in the water absorption ratio or the water absorption speed relative to pure water or water with a low ion content.

DISCLOSURE OF INVENTION

As a result of intensive investigations aimed at resolving the problems described above, the present inventors have found that a water absorbent material comprising a copolymer of an anhydropolyamino acid having at least one ethylenically unsaturated double bond within each molecule (A), and a water soluble monomer having an ethylenically unsaturated double bond (B) displayed a high level of water absorption capability relative to water incorporating a high concentration of salts, and as a result were able to complete the present invention.

In other words, the present invention provides a water absorbent material comprising a copolymer of an anhydropolyamino acid having at least one ethylenically unsaturated double bond within each molecule (A), and a water soluble monomer having an ethylenically unsaturated double bond (B).

The present invention also provides a water absorbent material comprising a copolymer of an anhydropolyamino acid having at least one ethylenically unsaturated double bond within each molecule (A), a water soluble monomer having an ethylene based unsaturated double bond (B), and a polysaccharide (C).

In addition, the present invention also provides an absorbent article comprising a liquid-permeable sheet, a liquid-impermeable sheet, and an absorber comprising a water absorbent material and a fiber material arranged between the liquid-permeable sheet and the liquid-impermeable sheet, wherein the water absorbent material is a water absorbent material comprising a copolymer of an anhydropolyamino acid having at least one ethylenically unsaturated double bond in a molecule (A) and a water soluble monomer having an ethylenically unsaturated double bond (B).

In addition, the present invention also provides an absorbent article comprising a liquid-permeable sheet, a liquid-impermeable sheet, and an absorber comprising a water absorbent material and a fiber material arranged between the liquid-permeable sheet and the liquid-impermeable sheet, wherein the water absorbent material is a water absorbent material comprising a copolymer of an anhydropolyamino acid having at least one ethylenically unsaturated double bond in a molecule (A), a water soluble monomer having an ethylenically unsaturated double bond (B), and polysaccharides (C).

BEST MODE FOR CARRYING OUT THE INVENTION

A detailed description of the water absorbent material according to the present invention is as follows.

First, the water absorbent material comprising a copolymer of an anhydropolyamino acid having at least one ethylenically unsaturated double bond in a molecule (A) (hereinafter referred to as a polymerizable anhydropolyamino acid (A)) and a water soluble monomer having an ethylenically unsaturated double bond (B) (hereinafter referred to as a water soluble polymerizable monomer (B)) will be explained.

Examples of the polymerizable anhydropolyamino acid (A) include those prepared by reacting an anhydropolyamino acid having no ethylenically unsaturated double bond in a molecule (A-1) (hereinafter referred to as an anhydropolyamino acid (A-1)) with a compound which has an ethylenically unsaturated double bond and a functional group having reactivity with the anhydropolyamino acid in a molecule (A-2) (hereinafter referred to as a polymerizable compound (A-2)) or those prepared by the polycondensation reaction of maleic amhydride, fumaric anhydride or malic anhydride and ammonia with heating.

Examples of the anhydropolyamino acid (A-1) include anhydrides of polyaspartic acid and polyglutamic acid. Among these anhydropolyamino acids, polysuccinimide as an anhydride of polyaspartic acid is preferred in view of industrial availability. These compounds may have a linear structure or a branched structure.

In addition, a basic skeleton of the anhydropolyamino acid (A-1) may contain a unit of an amino acid other than glutamic acid and aspartic acid.

Examples of the unit of the amino acid other than glutamic acid and aspartic acid include units of aliphatic α-amino acid such as glycine, alanine, valine, leucine, isoleucine, serine, threonine, asparagine, glutamine, lysine, ornithine, cysteine, cystine, methionine, proline, hydroxyproline, or arginine; aromatic α-amino acid such as tyrosine, phenylalanine, tryptophan, or histidine; α-amino acid whose side chain functional group is substituted; aminocarboxylic acid such as β-alanine or γ-aminobutyric acid; dipeptide (dimer) such as glycyl-glycine or aspartyl-phenylalanine; and tripeptide (trimer) such as glutathione. These amino acids may be optically active substances (L-isomer, D-isomer) or racemic modifications. These amino acid units may exist in the form of a random copolymer or a block copolymer after being combined with glutamic acid or aspartic acid.

There are no particular restrictions on the method of producing the aforementioned anhydropolyamino acid (A-1). Examples of suitable production methods include (1) heating D/L-aspartic acid and performing a dehydration condensation, (2) heating D/L-aspartic acid and performing a dehydration condensation in the presence of a catalyst such as phosphoric acid, (3) heating D/L-aspartic acid in a suitable solvent and in the presence of a catalyst such as phosphoric acid, and performing a dehydration condensation, (4) heating and reacting maleic anhydride, fumaric acid or malic acid with ammonia, and forming the anhydropolyamino acid via a maleimide or a maleamic acid intermediate, and (5) heating and reacting maleic anhydride, fumaric acid or malic acid with ammonia to generate a maleimide or a maleamic acid, and then producing the anhydropolyamino acid by further reaction in the presence of a catalyst such as phosphoric acid. A water absorbent material of the present invention can utilize an anhydropolyamino acid obtained from any of the above methods.

There are no particular restrictions on the polymerizable compound (A-2), although from the viewpoint of reactivity, compounds represented by the general formula [I] shown below are preferred.

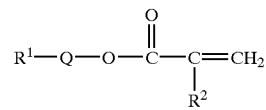

[I]

(wherein, $R^1$ represents at least one type of functional group selected from a group consisting of an amino group, an epoxy group, a carboxyl group, a carbodiimide group, an oxazoline group, an imino group and an isocyanate group, Q represents an alkylene group of 1 to 10 carbon atoms, and $R^2$ represents a hydrogen atom or an alkyl group of 1 to 4 carbon atoms.)

Examples of compounds represented by the by the aforementioned general formula [I] include glycidyl methacrylate, glycidyl acrylate, acrylic acid, methacrylic acid, 2-methacryloyloxyethyl isocyanate, and 2-isocyanatomethyl acrylate.

Examples of methods of reacting the anhydropolyamino acid (A-1) and the polymerizable compound (A-2) include (1) adding the polymerizable compound (A-2) directly to a powdered sample of the anhydropolyamino acid (A-1) and mixing; (2) dissolving the anhydropolyamino acid (A-1) in an aprotic organic solvent such as dimethyl formamide, dimethyl acetamide, N-methyl pyrrolidone, N,N'-dimethyl imidazolinone, dimethyl sulfoxide, or sulfolane, and then adding and mixing the polymerizable compound (A-2); (3) dispersing the anhydropolyamino acid (A-1) in a solvent such as cyclohexane, heptane, methanol, or acetone in which the anhydropolyamino acid (A-1) is insoluble, and then adding the polymerizable compound (A-2) to the dispersion and mixing; and (4) hydrolyzing the anhydropolyamino acid (A-1) by adding an alkali aqueous solution to the anhydropolyamino acid (A-1), and then adding the polymerizable compound (A-2) to the thus obtained aqueous solution and mixing.

The amount of the polymerizable compound (A-2) used should preferably be within a range from 0.8 to 3.0 mol, and more preferably be in a range from 0.9 to 2.0 mol per 1 mol of the anhydropolyamino acid (A-1). When the amount of the polymerizable compound (A-2) relative to the anhydropolyamino acid (A-1) is within a range from 0.8 to 3.0 mol, the amount of an unreacted substance can be reduced and formation of an insoluble substance and coloration due to secondary reaction can be prevented, thereby making it possible to inhibit factors which exert an adverse influence on the product.

When the amount of the polymerizable compound (A-2) is within the above range, the amount of an unreacted substance can be reduced and formation of an insoluble substance and coloration due to the crosslinking reaction as the secondary reaction can be prevented, thereby making it possible to inhibit factors which exert an adverse influence on the product.

Conditions of the reaction between the anhydropolyamino acid (A-1) and the polymerizable compound (A-2) are not specifically limited, but the reaction is preferably conducted at a temperature within a range from 20 to 150° C. The reaction time is preferably two hours or less.

The molecular weight of the resulting polymerizable anhydropolyamino acid (A) to be used in the present invention is preferably 500 or more in terms of weight-average molecular weight (hereinafter referred to as Mw), and more preferably 1000 or more. When the molecular weight is 500 or more, a water absorbent material having sufficiently enhanced water absorption properties to salts-containing water as the object of the present invention can be obtained.

A portion or all of the anhydropolyamino acid (A) is preferably hydrolyzed. An acidic amino acid residue, which is considered to enhance water absorption properties for salts-containing water, is formed by hydrolysis. The hydrolysis method is as described below.

As the water-soluble polymerizable monomer (B) used in the present invention, for example, there can be used ionic monomer such as (meth)acrylic acid and/or its alkali metal salt, alkali earth metal salt, or ammonium salt; nonionic monomer such as (meth)acrylamide, N,N-dimethylacrylamide, 2-hydroxyethyl (meth)acrylate, or N-methylol (meth)acrylamide; amino group-containing unsaturated monomer or its quaternized compound, such as diethylaminethyl (meth)acrylate or dimethylaminopropyl (meth)acrylate; carboxylic acids such as maleic acid, fumaric acid and itaconic acid; monoesters of unsaturated dicarboxylic acid and alcohol, such as monomethyl maleate, monoethyl maleate, monomethyl fumarate, monoethyl fumarate, monomethyl itaconate, and monoethyl itaconate; hydroxyl group-containing (meth)propyl (meth)acrylate such as 2-hydroxyethyl (meth)acrylate or 2-hydroxypropyl (meth)acrylate; hydroxyl group-containing vinyl ethers such as 2-hydroxyethyl vinyl ether, 3-hydroxypropyl vinyl ether, and 2-hydroxypropyl vinyl ether; sulfonic acid group-containing compound or its alkali metal salt, such as 2-sulfoethyl (meth)acrylate, 2-acrylamide-2-methylpropanesulfonic acid, 2-methacrylamide-2-methylpropanesulfonic acid, 2-sulfopropyl (meth)acrylate, or 2-sulfopropybutyl (meth)acrylate; and water-soluble polymerizable monomer having an ethylenically unsaturated double bond such as alkali earth metal salt or ammonium salt and a sulfonic acid group and/or a sulfonate group. These water-soluble polymerizable monomers can be used alone or in combination.

Examples of the alkali metal salt of (meth)acrylic acid and sulfonic acid include sodium salt, potassium salt, lithium salt, and rubidium salt. Among these alkali salts, sodium salt or potassium salt is preferred in view of the performances of the resulting polymer, industrial availability, and safety.

As used herein, the term "(meth)acrylic" means "acrylic" and "methacrylic". In these water-soluble polymerizable monomers, (meth)acrylic acid and/or its alkali metal salt, ammonium salt and (meth)acrylamide are preferred in view of water absorption properties.

Among these water-soluble polymerizable monomers, a water-soluble polymerizable monomer having an ethylenically unsaturated double bond such as alkali earth metal salt or ammonium salt and a sulfonic acid group and/or a sulfonate group (hereinafter referred to as a sulfonic acid group-containing polymerizable monomer) is preferably used because the water absorption properties as well as the water absorption ratio and the initial water absorption rate of pure water and water having a low ion content are not lowered.

In addition to the water-soluble polymerizable monomer (B), other hydrophobic monomers having an ethylenically unsaturated double bond can also be used as far as water absorption performances of the copolymer constituting the water absorbent material of the present invention are not impaired.

Examples of the other hydrophobic monomer having an ethylenically unsaturated double bond include various acrylic acid esters such as methyl acrylate, ethyl acrylate, butyl acrylate, and cyclohexyl acrylate; various methacrylic acid esters such as methyl methacrylate, ethyl methacrylate, n-butyl methacrylate, iso-butyl methacrylate, tert-butyl methacrylate, cyclohexyl methacrylate, and benzyl methacrylate; and various diesters of unsaturated carboxylic acid and alcohol, such as dimethyl fumarate, diethyl fumarate, dibutyl fumarate, dioctyl fumarate, dimethyl maleate, diethyl maleate, dibutyl maleate, dioctyl maleate, dimethyl itaconate, diethyl itaconate, dibutyl itaconate, and dioctyl itaconate. These hydrophobic monomers can be used alone or in combination.

The amount of the water-soluble polymerizable monomer (B) is usually within a range from 0.1/1 to 100/1 in terms of a weight ratio [water-soluble polymerizable monomer (B)/polymerizable anhydropolyamino acid (A)], and preferably from 1/1 to 50/1. When the amount of the water-soluble polymerizable monomer (B) is within the above range, a water absorbent material having excellent water absorption properties for salts-containing water can be obtained.

The copolymer of the water absorbent material of the present invention preferably comprises gel particles having a crosslinked structure introduced therein to enhance the strength of the copolymer. When the quantity of the crosslinked structure in the copolymer increases, it becomes possible to enhance the strength of the copolymer. On the other hand, when the quantity of the crosslinked structure decreases, it becomes possible to enhance water absorption properties. Therefore, the gel strength and water absorption properties of the copolymer can be adjusted by appropriately controlling the crosslinked structure.

The gel strength of the water absorbent material of the present invention is preferably 0.1 $g/cm^2$ or more, the upper limitation being a numerical value where desired water absorption properties can be obtained. The gel strength is based on the numerical value measured by the "method of measuring the gel strength" described hereinafter.

Examples of the method of preparing gel particles include (1) a method of irradiating the copolymer used in the water absorbent material of the present invention with active radiation such as electron beams, radiation or the like and (2) a method of using a crosslinking agent.

Examples of the crosslinking agent include crosslinkable monomers having at least two ethylenically unsaturated double bonds, crosslinkable monomer having at least two reactive groups, and crosslinking agents other than these crosslinking agents.

As the crosslinkable monomer having at least two ethylenically unsaturated double bonds, any monomer having two or more ethylenically unsaturated double bonds and examples thereof include N,N'-methylenebis (meth) acrylamide, (poly)ethylene glycol di(meth)acrylate, (poly) propylene glycol di(meth)acrylate, trimethylolpropane tri (meth)acrylate, trimethylolpropane di(meth)acrylate, glycerin tri(meth)acrylate, glycerin acrylate methacrylate, ethylene oxide-modified trimethylolpropane tri(meth) acrylate, pentaerythritol tetra(meth)acrylate, dipentaerythritol hexa(meth)acrylate, triallyl cyanurate, triallyl isicyanurate, triallyl phosphate, triallylamine, poly(meth)

allyloxyalcane, (poly)ethylene glycol diglycidyl ether, glycerol diglycidyl ether, ethylene glycol, polyethylene glycol, propylene glycol, glycerin, pentaerythritol, ethylenediamine, polyethyleneimine, and glycidyl (meth) acrylate.

Examples of the crosslinkable monomer having at least two reactive groups include polyhydric alcohol such as ethylene glycol, diethylene glycol, triethylene glycol, polyethylene glycol, glycerin, polyglycerin, propylene glycol, 1,4-butanediol, 1,5-pentanediol, 1,6-hexanediol, neopentyl alcohol, diethanolamine, tridiethanolamine, polypropylene glycol, polyvinyl alcohol, pentaerythritol, sorbitol, sorbitan, glucose, manntiol, mannitane, sucrose, or glucose; polyglycidyl ether such as ethylene glycol glycidyl ether, polyethylene glycol glycidyl ether, or glycerin triglycidyl ether; haloepoxy compound such as epichlorohydrin or α-methylchlorohydrin; polyaldehyde such as glutalaldehyde or glyoxazol; polyamines such as ethylenediamine; and hydroxide, halide, carbonate, oxide, borate (e.g. borax, etc.) or polyvalent metal compound (e.g. aluminum isopropylate, etc.) of a metal of the group IIA, IIIB and VIII of the Periodic Table, such as calcium hydroxide, calcium chloride, calcium carbonate, calcium oxide, borax magnesium chloride, magnesium oxide, aluminum chloride, zinc chloride, or nickel chloride.

These compounds can be used alone or in combination, taking reactivity into consideration.

The amount of the crosslinkable monomer having at least two ethylenically unsaturated double bonds or the crosslinkable monomer having at least two reactive groups is preferably within a range from 0.005 to 2 mol %, and more preferably from 0.01 to 1 mol %, based on the water-soluble polymerizable monomer (B). When the amount is within a range from 0.005 to 2 mol %, a water absorbent material having a good balance between the water absorption properties and gel strength can be obtained.

Examples of the crosslinking agent include diglycidyl ether compound, haloepoxy compound, polyamine compound, and isocyanate compound.

Examples of the diglycidyl ether compound include ethylene glycol diglycidyl ether, propylene glycol diglycidyl ether, and glycerin-1,3-diglycidyl ether. Examples of the haloepoxy compound include epichlorohydrin and β-methylepichlorohydrin. Examples of the polyamine compound include chain aliphatic polyamine such as ethylenediamine, diethylenetriamine, triethylenetetramine, tetraethylenepentamine, pentaethylenehexamine, hexamethylenediamine, or polyether polyamine; cyclic aliphatic polyamine such as menthenediamine, isophoronediamine, or bis(4-aminocyclohxyl)methane-3,9-bis(3-aminopropyl)-2,4,8,10-tetraoxanepyro[5,5]-undecane; aromatic polyamine such as m-xylenediamine or p-xylenediamine; polyamides obtained from dimer acid and an aliphatic polyamine; and basic amino acid such as lysine.

Examples of the isocyanate compound include tolylene diisocyanate (TDI), phenylene diisocyanate (PPDI), diphenylmethane diisocyanate (MDI), hydrogenated MDI, polymeric MDI, tolidine diisocyanate (TODI), hexamethylene diisocyanate (HDI), isophorone diisocyanate (IPDI), xylylene diisocyanate (XDI), lysine diisocyanate (LDI), tetramethylenexylene diisocyanate (TMXDI), triphenylmethane triisocyanate, tris(isocyanatephenyl) thiophosphate, undecane triisocyanate, lysine ester triisocyanate, 1,8-diisocyanate-4-isocyanate methyloctane, bicycloheptane triisocyanate, and urethane-modified compounds thereof, alophanate-modified compound, buret-modified compound, isocyanurate-modified compound, carbodimide-modified compound, block isocyanate, and mixtures thereof. These compound may be used alone or in combination.

The crosslinking agent is preferably used as long as water absorption properties of the water absorbent material are not impaired, and the amount is usually within a range from 0.1 to 60 mol %, and preferably from 1 to 50 mol %, based on the imide ring of the anhydropolyamino acid.

The crosslinkable monomer is used in the reaction between the polymerizable anhydropolyamino acid (A) and the water-soluble polymerizable monomer (B). The crosslinking agent is preferably added during or after the reaction between the polymerizable anhydropolyamino acid (A) and the water-soluble polymerizable monomer (B).

The water absorbent material comprising a copolymer of the polymerizable anhydropolyamino acid (A), the water-soluble polymerizable monomer (B) and polysaccharides (C) will now be described.

In the copolymer constituting the water absorbent material of the present invention, a moiety having high non-ionicity is introduced by using polysaccharides (C) as a copolymer component, thereby making it possible to further enhance water absorption properties to salts-containing water.

Examples of the method of copolymerizing polysaccharides (C) with the polymerizable anhydropolyamino acid (A) and the water-soluble polymerizable monomer (B) include (1) a method of ring-opening polysaccharides in the presence of an azo catalyst, thereby to activate carbon atoms to which hydroxyl groups are attached and to graft-copolymerize carbon atoms with unsaturated double bonds and (2) a method of using a crosslinking agent capable of reacting with the respective functional groups of the polymerizable anhydropolyamino acid (A), the water-soluble polymerizable monomer (B) and polysaccharides. The copolymer of the water absorbent material of the present invention obtained by any method can be used.

Examples of polysaccharides (C) include starch, cellulose, and alginic acid.

Examples of the starch include starches made of amylose and/or amylopectin originating in natural substances or plants, starch-containing substances, and modified substances thereof. Specific examples thereof include potato starch, corn starch, wheat starch, tapioca starch, rice starch, sweet potato starch, sago starch, waxy corns, high amylose corns, wheat flour, and rice flour. As the modified starch, for example, there can be used those obtained by graft copolymerization of starch and acrylic acid ester, methacrylic acid ester, olefin or styrene, those obtained by reacting starch with fatty acid, and those obtained by conversion starch into dextrin or oxidation, pregeklatinization treatment, etherification, esterification or crosslinking of starch. In addition, a structure-modified starch obtained by heating hydrous starch to a temperature higher than its glass transition temperature and melting point (described in EP-A-327505) is also included. Furthermore, polysaccharides such as guar gum, chitin, chitosan, cellulose, alginic acid, and agar can be used.

Examples of the cellulose include celluloses obtained from wood materials, leaves, stems, basts and seed fibers; and processed celluloses such as alkyl-etherified cellulose, organic acid-esterified cellulose, carboxymethylated cellulose, cellulose oxide, and hydroxyalkyl-etherified cellulose.

The amount of polysaccharides (C) is usually 10/1 or less in terms of a weight ratio [polysaccharides (C)/polymerizable anhydropolyamino acid (A)], and preferably 5/1 or less. By using polysaccharides (C) within the above range, it becomes possible to obtain the effect that the water absorbent material has non-ionicity.

Similar to the water absorbent material, the monomer having at least two ethylenically unsaturated double bonds or the crosslinkable monomer having at least two reactive groups and the curing agent can be used as the monomer component of the copolymer.

The method of preparing the copolymer constituting the water absorbent material of the present invention will now be described.

The method of preparing the copolymer can be conducted by a well-known method. That is, there can be used any method such as (1) a method of charging a polymerizable anhydropolyamino acid (A) and a water-soluble polymerizable monomer (B) in a reaction vessel at a time, mixing them and reacting the mixture or (2) a method of initiating the reaction of one component and adding the other component dropwise. In the present invention, this is not specifically limited.

It is preferred in view of uniform reaction that polysaccharides (C) be previously dissolved or swollen and dispersed in a system before the reaction.

In the case of reacting the polymerizable anhydropolyamino acid (A) with the water-soluble polymerizable monomer (B), although a method of polymerizing by irradiation with radiation, electron beams, or ultraviolet rays, can be employed, a polymerization method using a radical polymerization initiator is industrially preferred. Specific examples of the radical polymerization initiator include inorganic peroxide such as hydrogen peroxide, ammonium persulfate, potassium persulfate, or sodium persufate; organic peroxide such as benzoyl peroxide, di-t-butylperoxide, cumenehydroxy peroxide, succinic acid peroxide, or di(2-ethoxyethyl) peroxycarbonate; azo compound such as azobisisobutyronitrile, azobiscyanovaleric acid, or 2,2'-azobis(2-aminodipropane) hydrochloride; and redox catalyst (made of a combination of a reducing agent such as sulfite or hyposulfite of alkali metal, ammonium sulfite, ammonium bisulfite or ascorbic acid and an oxidizing agent such as persulfate of alkali metal, ammonium persulfate, or peroxide. These radical polymerization initiators may be used alone or in combination.

The amount of the radical polymerization initiator is usually within a range from 0.0001 to 5% by weight, and preferably from 0.0005 to 1% by weight, based on the total amount of the water-soluble polymeriable monomer (B) and the crosslinking agent.

In the polymerization reaction, hydrophilic polymers such as polyacrylic acid or its salt, crosslinked substance thereof, polyvinyl pyrrolidone, and polyvinyl alcohol; chain transfer agents such as hypophosphorous acid and alkylmercaptan; surfactants; and blowing agents such as carbonate, dry ice, and azo compound can be added.

The polymerization reaction may be conducted in an aqueous solution, a solvent and a suspension, and is not specifically limited.

In the case in which the polymerization reaction is conducted in an aqueous solution, it is preferred to previously hydrolyze the polymerizable anhydropolyamino acid (A).

The hydrolysis reaction is conducted by an aqueous solution of an alkali metal compound and/or an alkali earth metal compound under the conditions that the reaction temperature is usually within a range from 0 to 100° C., and preferably from 20 to 50° C. The reaction time is not specifically limited, but is usually 20 hours or less, preferably 10 hours or less, and particularly preferably 2 hours or less, in view of the productivity.

Typical examples of the alkali metal compound or the alkali earth metal compound include hydroxide and carbonate of the alkali metal and alkali earth metal. Specific examples thereof include lithium hydroxide, sodium hydroxide, potassium hydroxide, magnesium hydroxide, calcium hydroxide, lithium carbonate, sodium carbonate, potassium carbonate, magnesium carbonate, and calcium carbonate. Generally, an aqueous 0.1–40% wt % solution of sodium hydroxide or potassium hydroxide is used. The amount of the alkali compound added is an amount corresponding to 0.4 to 1 mol per mol of the imide ring group.

In the case in which the polymerization reaction is conducted in a solvent, the components are dissolved in the solvent. Examples of the solvent include aprotic organic solvents such as dimethylformamide, dimethylacetamide, N-methylpyrrolidone, N,N-dimethylimidazolione, dimethyl sulfoxide, and sulfolane.

In the case in which the polymerization reaction is conducted in a suspension, a reverse phase suspension polymerization method can be used.

The reverse phase suspension polymerization method will now be described.

Examples of the reverse phase suspension polymerization method include (1) a method of reverse phase suspension polymerization of an aqueous mixed solution of a polymerizable anhydropolyamino acid (A) and a water-soluble polymerizable monomer (B) in a hydrophobic solvent containing a water-in-oil type (hereinafter referred to as W/O type) surfactant in the presence of a crosslinking agent, using a water-soluble radical polymerization initiator; (2) a method of initiating reverse phase suspension polymerization of a water-soluble polymerizable monomer (B) in a hydrophobic solvent containing a W/O type surfactant in the presence of a crosslinking agent, using a water-soluble radical polymerization initiator, and further conducting reverse phase suspension polymerization by adding dropwise an aqueous solution of a polymerizable anhydropolyamino acid (A); and (3) a method of conducting first-stage reverse phase suspension polymerization of an aqueous solution of a water-soluble polymerizable monomer (B) in a hydrophobic solvent containing a W/O type surfactant in the presence of a crosslinking agent, using a water-soluble radical polymerization initiator, and further conducting reverse phase suspension polymerization by adding a mixed solution of a polymerizable anhydropolyamino acid (A) and the water-soluble polymerizable monomer (B). In the case of the copolymer constituting the water absorbent material of the present invention, any reverse phase suspension polymerization method can be used.

This reverse phase suspension polymerization method is a preferred method because a bead-like water absorbent material capable of being easily ground can be obtained by using a surfactant.

Specific method of preparing a copolymer by the reverse phase suspension polymerization method using a sulfonic acid group-containing polymeriable monomer as the water-soluble polymerizable monomer (B) will now be described.

An aqueous solution of a sulfonic acid group-containing polymerizable monomer (B) is prepared by adding and dissolving a crosslinking agent and a radical polymerization initiator and, if necessary, a water-soluble chain transfer agent such as thiols, thiol acids, secondary alcohols, amines or hypophosphites in an aqueous solution containing a previously neutralized sulfonic acid group-containing polymerizable monomer and the other monomer having ethylenically unsaturated double bonds, and then the resulting solution is deaerated by introducing an inert gas such as nitrogen. In a polymerization apparatus, a surfactant is charged in a hydrophobic solvent and is optionally dissolved by heating, and then aeration is conducted by introducing a nitrogen gas into the apparatus. The aqueous solution of the sulfonic acid group-containing polymerizable polymer is poured into the apparatus and temperature rising is initiated under stirring. During temperature rising, the aqueous solution is converted into water droplets, which are suspended while being dispersed in the hydrophobic solvent. With the temperature rising, heat is generated and the polymerization is initiated.

The method of adding the polymerizable anhydropolyamino acid (A) is not specifically limited, but includes, for example, (1) a method of previously mixing an aqueous solution of a previously hydrolyzed polymerizable anhydropolyamino acid (A) with an aqueous solution of a sulfonic acid group-containing polymerizable monomer, (2) a method of simultaneously pouring an aqueous solution of a sulfonic acid group-containing polymerizable monomer, (3) a method of pouring during temperature rise, or (4) a method of pouring after the polymerization was initiated by heat generation. Among these methods, the method (4) is preferred because it can maintain the stability of the system more satisfactorily.

In the case in which the aqueous solution of the polymerizable anhydropolyamino acid (A) is added after the polymerization was initiated by heat generation, it may be added as it is.

Since there sometimes arise a problem that polymer particles agglomerate according to the amount of the polymerizable anhydropolyamino acid (A), an inert solvent containing a surfactant dissolved therein is added to an aqueous solution of the polymerizable anhydropolyamino acid (A) and the polymerizable anhydropolyamino acid (A) is dispersed in the inert solvent by stirring, and then the resulting dispersion is preferably added to a polymer solution.

Although timing of pouring after heat generation is not specifically limited, pouring is conducted during the time immediately after heat generation and the time after three hours have passed since heat generation, and particularly preferably during the time immediately after heat generation and the time after two hours have passed since heat generation. Pouring is preferably conducted during the above timing range because the aqueous solution of the polymerizable anhydropolyamino acid (A) can be incorporated into particles of the copolymer, which is being formed in the reaction system, without separating the aqueous solution.

After initiation of the polymerization, cooling is appropriately conducted according to the state of heat generation. The temperature of the polymerization reaction is preferably within a range from 60 to 100° C., and particularly preferably from 60 to 80° C.

The rotation number of a stirring blade of a reaction apparatus during the reaction cannot be shown unambiguously because the absolute value thereof varies depending on the kind of the stirring blade and the size of the polymerization reaction vessel, but is preferably within a range from 50 to 500 rpm in view of the polymerization safety.

The suspension polymerization reaction yields a slurry mixture containing particles having an average particle diameter within a range from 10 to 300 μm (hydrous gel particles/excess surfactant/hydrophobic solvent).

The slurry mixture is converted into copolymer particles by direct dehydration according to a publicly known procedure or azeotropic dehydration with a hydrophobic solvent and optionally subjecting to a surface treatment, followed by drying and various steps such as screening.

As the W/O type surfactant used in the present invention, any surfactant can be used as long as it is soluble in a hydrophobic solvent or it has hydrophilicity and is capable of forming a W/O type emulsion system.

The surfactant having such properties is a nonionic or anionic surfactant which generally has a HLB value within a range from 1 to 9, and preferably from 2 to 7. Specific examples of the surfactant include sorbitan fatty acid ester, polyoxysorbitan fatty acid ester, sucrose fatty acid ester, polyglycerin fatty acid ester, polyoxyethylene alkyl phenyl ether, ethylcellulose, ethylhydroxyethylcellulose, polyethylene oxide, maleic anhydride modified polyethylene, maleic anhydride modified polybutadiene, maleic anhydride modified ethylene-propylene-diene-terpolymer, copolymer of α-olefin and maleic anhydride or derivative thereof, and polyoxyethylene alkyl ether phosphoric acid.

The amount of the surfactant is within a range from 0.05 to 10% by weight, and preferably from 0.1 to 1% by weight.

As the hydrophobic solvent, any solvent can be used as long as it is basically insoluble in water and is inert with respect to the polymerization reaction. Examples thereof include aliphatic hydrocarbons such as n-pentane, n-hexane, n-heptane, or n-octane; and aromatic hydrocarbons such as benzene, toluene, or xylene. Among these solvents, n-hexane, n-heptane and cyclohexane are particularly preferred because a non-greasy water absorbent material can be obtained.

The amount of these hydrophobic solvents is usually 0.5 to 10 times larger than that of the aqueous solution of the water-soluble polymerizable monomer (B) used in the first-stage reaction in the reverse phase suspension polymerization method (3).

The reaction operation may be conducted in atmospheric air, but is preferably conducted in an inert gas atmosphere to inhibit the secondary reaction. The reaction pressure is not specifically limited, but is preferably a reduced pressure below normal pressure, and particularly preferably is a highly reduced pressure. Specifically, it is preferably within a range from 10 to $1.013 \times 10^5$ Pa.

The reaction time is not specifically limited, but is usually 100 hours or less, preferably 50 hours or less, and more preferably 20 hours or less.

The method of preparing the copolymer used in the water absorbent material of the present invention using the reaction apparatus includes, for example, a preparation method using a publicly known reaction apparatus and specific examples thereof include (1) a method of polymerizing while stirring optionally in a twin-bowl kneader, (2) a method of cast-polymerizing in a container and (3) a method of standing-polymerizing by continuously feeding on a driving belt. The water absorbent material of the present invention can be prepared by any method, in addition to the preparation methods using the apparatus.

To optimize water absorption properties, about 5 to 100 mol %, preferably 65 to 80 mol % of acid groups in the water-soluble polymerizable monomer (B) is preferably neutralized with an alkali compound before or after the reaction.

The alkali compound used herein is preferably a hydroxide or a carbonate of an alkali metal salt or an alkali earth metal salt. Examples of the compound include lithium hydroxide, sodium hydroxide, potassium hydroxide, magnesium hydroxide, calcium hydroxide, lithium carbonate, sodium carbonate, potassium carbonate, magnesium carbonate, and calcium carbonate.

The water absorbent material of the present invention varies depending on the method of the copolymerization reaction of the copolymer. In case of the reaction of an aqueous solution, the water absorbent material can be prepared by granulating hydrous gel particles made of the copolymer after the reaction, and passing through a series of steps such as drying step, grinding step, screening step, surface crosslinking treatment step and screening step.

To dry hydrous gel particles obtained through the above steps, hydrous gel particles are preferably granulated to form granules having a predetermined particle diameter in order to enhance the drying efficiency by increasing the surface area. Hydrous gel particles are granulated simultaneously by polymerizing while stirring with a twin-bowl kneader, or by extruding polymerized hydrous gel particles through a die using a meat grinder. Hydrous gel particles can also be granulated by a cutting mill. Although the particle diameter of granulated gel particles can be appropriately adjusted by a drier, but an average particle diameter is preferably within a range from 0.1 to 10 mm. When the average particle diameter is less than 0.1 mm, physical properties of the water absorbent material are likely to be lowered. On the other hand, when the average particle diameter exceeds 10 mm, granulated gel particles are not easily dried and, therefore, it is not preferred.

On granulation of hydrous gel particles made of the copolymer, gel coarse particles having an average particle diameter of larger than 10 mm and gel fine particles having an average particle diameter of smaller than 0.1 mm are likely to be formed. The gel coarse particles and gel fine particles can be reused by adding to the aqueous solution of the water-soluble polymerizable monomer (B) and polymerized gel particles after screening and recovering.

Gel particles granulated in the granulating step are dried in the following drying step. In the drying method, for example, a hot-air drier, air-current drier, a fluidized bed drier, a drum drier, microwave drier, a far infrared drier and a vacuum drier can be appropriately used.

Hydrous gel particles obtained in the drying step are ground and screened according to uses of the water absorbent material in the following grinding step and screening step to form granules having a predetermined particle size. When used in a diaper, napkin or the like, the screened granules have a particle size of 1 mm or less, and preferably 0.85 mm or less. To sufficiently exert water absorption performances in the diaper or sanitary napkin, fine powders having a particle diameter of 105 μm or less, preferably 212 μm or less, and more preferably 300 μm or less are preferably removed by screening. Fine powders recovered in the grinding step and screening step can be reused by adding in the polymerizing step and drying step.

The vicinity of the surface of the water absorbent material of the present invention can be crosslinked by using a surface crosslinking agent having two or more functional groups capable of reacting with functional groups of the copolymer constituting the water absorbent material.

Specifically, the water absorbent material of the present invention is mixed with the surface crosslinking agent, and then the vicinity of the surface of the water absorbent material is crosslinked by a heat treatment.

Examples of the surface crosslinking agent include polyhydric alcohol such as diethylene glycol, propylene glycol, triethylene glycol, tetraethylene glycol, polyethylene glycol, 1,3-propanediol, dipropylene glycol, 2,3,4-trimethyl-1,3-pentanediol, polypropylene glycol, glycerin, polyglycerin, 2-butene-1,4-diol, 1,4-butanediol, 1,5-pentanediol, 1,6-hexanediol, 1,2-cyclohexanedimethanol, 1,2-cyclohexanediol, trimethlolpropane, diethanolamine, triethanolamine, polyoxypropylene, oxyethylene-oxypropylene block copolymer, pentaerythritol, or sorbitol; epoxy compound such as ethylene glycol diglycidyl ether, polyethylene glycol diglycidyl ether, glycerol polyglycidyl ether, diglycerol polyglycidyl ether, polyglycerol polyglycidyl ether, propylene glycol diglycidyl ether, polypropylene glycol diglycidyl ether, or glycidol; polyhydric amine compound such as ethylenediamine, diethylenetriamine, triethylenetetramine, tetraethylenepentamine, pentaethylenehexamine, polyethyleneimine, or polyamide-polyamine; haloepoxy compound such as epichlorohydrin, epibromohydrin, or α-methylepichlorohydrin; condensate of the above polyvalent amine compound and the above haloepoxy compound; polyhydric isocyanate compound such as 2,4-tolylene diisocyanate or hexamethylene diisocyanate; polyhydric oxazoline compound such as 1,2-ethylenebisoxazoline; silane coupling agent such as γ-glycidoxypropyltrimethoxysilane or γ-aminopropyltrimethoxysilane; alkylene carbonate compound such as 1,3-dioxolan-2-one, 4-methyl-1,3-dioxolan-2-one, 4,5-dimethyl-1,3-dioxolan-2-one, 4,4-dimethyl-1,3-dioxolan-2-one, 4-ethyl-1,3-dioxolan-2-one, 4-hydroxymethyl-1,3-dioxolan-2-one, 1,3-dioxan-2-one, 4-methyl-1,3-dioxan-2-one, 4,6-dime 1,3-dioxan-2-one, 1,3-dioxan-2-one, or 1,3-dioxoban-2-one; and polyhydric metal compound such as hydroxide or chloride of zinc, calcium, magnesium or aluminum. Among these surface crosslinking agents, polyhydric alcohol compound, epoxy compound, polyhydric amine compound, condensate of polyvalent amine compound and haloepoxy compound, and alkylene carbonate compound are preferred in view of the reactivity and safety. These surface crosslinking agents may be used alone or in combination.

The amount of the surface crosslinking agent relative to the water absorbent material varies depending on the combination of the water absorbent material and the surface crosslinking agent, but is usually within a range from 0.01 to 10 parts by weight, and preferably from 0.05 to 3 parts by weight, based on 100 parts by weight of the copolymer in the dry state. By using the surface crosslinking agent in the amount within the above range, water absorption properties for body fluids (aqueous liquids) such as urine, sweat or menstrual blood can be further improved.

In the case in which the water the water absorbent material is mixed with the surface crosslinking agent, water is preferably used. The amount of water varies depending on the kind, the particle size and the water content of the water absorbent material, but is usually within a range from 0.5 to 10 parts by weight, and preferably from 0.5 to 3 parts by weight, based on 100 parts by weight of the solid content of the water absorbent material, thus making it possible to form a crosslinking layer having a sufficient thickness in the vicinity of the surface.

In the case in which the water the water absorbent material is mixed with the surface crosslinking agent, a hydrophilic organic solvent may be used. Examples of the hydrophilic organic solvent include lower alcohol such as methyl alcohol, ethyl alcohol, propyl alcohol, isopropyl alcohol, butyl alcohol, isobutyl alcohol, or t-butyl alcohol; ketones such a acetone; ethers such as dioxane, alkoxy (poly)ethylene glycol, or tetrahydrofuran; amides such as N,N-dimethylformamide; and sulfoxides such as dimethyl sulfoxide.

The amount of the hydrophilic organic solvent varies depending on the kind and particle size of the water absorbent material, but is usually within a range from 0.001 to 10 parts by weight, and preferably from 0.1 to 5 parts by weight, based on 100 parts by weight of the water absorbent material.

It is necessary that a preferred mixer used to mix the surface crosslinking agent with the water absorbent material is capable of producing a large mixing force to ensure uniform mixing. Preferred examples of the mixer include a cylindrical mixer, double wall conical mixer, high-speed stirring mixer, V-shaped mixer, ribbon-shaped mixer, screw mixer, flow furnace rotary disk type mixer, air-current mixer, twin-bowl kneader, internal mixer, grinding mixer, rotary mixer, and screw extruder.

The temperature of the heat treatment is preferably within a range from 80 to 300° C. When the temperature is within the above range, more uniform crosslinking can be achieved, thereby making it possible to obtain a water absorbent material, which is capable of reducing the amount of a soluble component eluted and has excellent water absorption properties.

As the apparatus for heat treatment, for example, a publicly known drier or heating furnace can be used. Specific examples thereof include groove mixing drier, rotary drier, disk drier, fluidized bed drier, air-current drier, infrared drier, and vacuum drier.

The water absorbent material of the present invention is superior in water absorption properties to pure water and salts-containing water, especially water absorption properties to salts-containing water.

Water absorption performances can be determined by the method of testing water absorption of a high water absorbent material using a tea bag method defined in Japanese Industrial Standard (JIS K7223). In the case of evaluating by the tea bag method, the water absorbent material of the present invention has water absorption performances of 20 times or more to ion exchange water and has water absorption performances of 5 times or more to a physiological saline (aqueous 0.9% sodium chloride solution).

The water absorbent material of the present invention can be applied to all purposes that have conventionally been known. The water absorbent material can be used in the fields, for example, sanitary field such as sanitary products (e.g. diapers, sanitary napkins, etc.), medical field such as poultices, civil engineering and construction field such as sludge gelling agents, food field, industrial field, and agricultural/horticultural field such as soil conditioners and water-storing materials and its utility value is remarkably great. Other purposes include water-swelling rubber prepared by incorporating a rubber into the water absorbent material.

The absorbent article of the present invention will now be described.

The liquid-permeable sheet constituting the absorbent article of the present invention means a sheet made of a material which is permeable to an aqueous liquid, and examples thereof include nonwoven fabric, woven fabric, and synthetic films made of a material such as polyethylene, polypropylene, or polyamide.

The liquid-impermeable sheet constituting the absorbent article of the present invention means a sheet made of a material which is impermeable to an aqueous liquid, and examples thereof include synthetic films made of a material such as polyethylene, polypropylene, ethylene vinyl acetate, or polyvinyl chloride, and a film made of a composite of the synthetic resin and a nonwoven fabric or a woven fabric.

The liquid-impermeable sheet constituting the absorbent article of the present invention can use the above water absorbent material.

Examples of the fiber material constituting the water absorbent material include hydrophobic fiber material and hydrophilic fiber material. Among these fiber materials, hydrophilic fiber material is preferred in view of superior affinity with the solution to be absorbed. Examples of the hydrophilic fiber material include cellulose fiber such as mechanical pulp or semi-chemical pulp obtained from wood materials; artificial cellulose fiber such as rayon or acetate; and fiber material obtained by hydrophilization of thermoplastic fiber. The fiber material may have a fibrous shape, or may be formed into a sheet such as tissue paper or pulp mat.

The absorbent article of the present invention comprises a liquid-permeable sheet, a liquid-impermeable sheet, and an absorber comprising the water absorbent material, and a fiber material arranged between the liquid-permeable sheet and the liquid-impermeable sheet, and has a structure such that the absorber is supported inside. Specific examples of the method of producing the absorbent article include a method of sandwiching the absorber between the liquid-permeable sheet and the liquid-impermeable sheet and bonding an outer peripheral portion of the liquid-permeable sheet and the liquid-impermeable sheet using an adhesive such as hot-melt adhesive or a bonding means such as a heat seal.

The method of producing an absorber comprising a water absorbent material and a fiber material is not specifically limited, but includes (1) a method of forming a fiber material into a sheet and covering a water absorbent material with the sheet, (2) a method of dispersing a water absorbent material over a multi-layer fiber sheet and forming the multi-layer sheet, and (3) a method of mixing a fiber material with a water absorbent material and forming the mixture into a sheet.

The absorbent article of the present invention is used in disposable diapers for infants, adults, and persons suffering from incontinence, and sanitary napkins. The absorbent article is particularly suited for use in disposable diapers for adults, wherein a swelling gel of the water absorbent material is drastically deteriorated due to a large amount of excretion and long time in contact with urine, among these uses because of its excellent absorbency of urine and body fluids as well as excellent urine leakage inhibition effect.

EXAMPLES

The following Examples further illustrate the present invention in detail, but the present invention is not limited by the Examples. In the following Examples, percentages are by weight unless otherwise specified. Various characteristics of the resin of the present invention were determined by the following methods.

[Method of Measuring Water Absorption Ratio]

The water absorption capability of resins obtained in the Examples of the present invention was determined in accordance with the method of testing water absorption of a high water absorbent material described in Japanese Industrial Standard JIS K7223. 0.20 g (1.00 g based on an aqueous 0.9% sodium chloride solution) of a dry resin was put in a tea bag (200 mm×100 mm) made of a 255 mesh nylon gauze and the resin was swollen by dipping in 1000 ml of ion exchange water or an aqueous 0.9% sodium chloride solution for a fixed time. After pulling out the tea bag, the solution was drained off and the weight was measured. The same operation was repeated, except that only the tea bag was used and the weight of the tea bag was measured. The resulting weight was taken as the blank. The water absorption ratio W (g/g) was calculated in accordance with the following equation:

$$W = \frac{b_{60\min} - c - a}{a}$$

where W is water absorption ratio (g/g), a is a weight (g) of a sample, b is a weight (g) of the sample measured after a tea bag containing the sample was dipped for a predetermined time and the solution was drained off, and c is an average value of a weight (g) of the sample measured after a tea bag containing no sample was dipped for a predetermined time and the solution was drained off.

[Method of Measuring Water Absorption Rate]

A stirrer tip was rotated at about 600 rpm in 50 g of an aqueous 0.9% sodium chloride solution in a 100 ml glass beaker and then 2 g of a sample was put in the beaker along with the inner wall thereof. Then, a resin was added and the time (in seconds), which is required for the resin to be swollen by water absorption, thereby stopping rotation of the stirrer tip, was taken as the water absorption rate.

[Method of Measuring Gel Strength]

1.0 g of a crosslinked resin was allowed to absorb 100 g of pure water (water absorption by 100 times) and a dead-weight was placed on the resin after water absorption. The total weight of the dead-weight per unit area (g/cm$^2$) when the dead-weight placed first on the resin was taken as a gel strength.

Synthetic Example 1

In a 2 L round bottom flask, 100 g of L-aspartic acid and 50 g of 85% phosphoric acid were charged and the reaction was conducted under reduced pressure in an oil bath at a bath temperature of 200° C. for four hours using an evaporator. The resulting product (25 g) was washed several times with water and methanol to obtain polysuccinimide. As a result of the measurement of gel permeation chromatography (hereinafter referred to as GPC), this polysuccinimide has a Mw of 20,000.

Synthetic Example 2

In a 1 L four-necked flask equipped with a stirrer, a thermometer, a reflux condenser, and a nitrogen gas introducing device, 96 g of maleic anhydride and 50 g of ion exchange water were added and, after dissolving maleic anhydride by heating to 55° C., the solution was cooled to obtain a slurry of maleic anhydride. When the temperature of the system reached 55° C. as a result of heating, 60.8 g of 28% ammonia water was added. The system was heated to 80° C. and, after the reaction was conducted for three hours, the resulting aqueous solution was dried to obtain a reaction intermediate. In a 2 L round bottom flask, 100 g of the reaction intermediate and 10 g of 85% phosphoric acid were charged and the reaction was conducted under reduced pressure in an oil bath at a bath temperature of 200° C. for four hours using an evaporator. The resulting product was washed several times with water and methanol to obtain polysuccinimide. The Mw of this polysuccinimide was measured by GPC. As a result, it was 3,000.

Example 1

In a 500 ml four-necked flask equipped with a stirrer, a thermometer, a reflux condenser and a nitrogen gas introducing device, 10 g of polysuccinimide obtained in Synthetic Example 1 and 20 g of N,N-dimethylformamide (hereinafter referred to as DMF) were charged and dissolved at about 60° C., and furthermore, 0.5 g of 2-methacryloyloxyethyl isocyanate was added. As a result, heat was generated. After the reaction was continued for 30 minutes, 150 g of an aqueous solution containing 3.3 g of sodium hydroxide dissolved therein was added and polysuccinimide was hydrolyzed. After the temperature in the system was reduced to about 35° C., 1 g of "ALSTAR B" (pregelatinized starch, manufactured by NIHON SHOKUHIN KAKO CO., LTD.), 25 g of acrylic acid and 0.25 g of dipentaerythritol hexamethacrylate were charged. After the atmosphere in the system was replaced by a nitrogen gas, 7.5 mg of 2,2-azobisaminodipropane dihydrochloride, 5 mg of ascorbic acid and 57 mg of an aqueous hydrogen peroxide (35%) solution were respectively dissolved in 1 g of ion exchange water. The resulting solutions were added to the above aqueous solution in this sequence and the reaction was initiated, and then the mixture was maintained at about 60° C. for three hours (hereinafter referred to as (1) first step). 2.4 g of hexamethylenediamine was dissolved in 20 g of ion exchange water and the resulting solution was added to the above aqueous solution, and then the reaction was conducted. Furthermore, 10.4 g of sodium hydroxide was dissolved in 30 g of ion exchange water and the resulting solution was added, thereby to neutralize carboxyl groups originating in acrylic acid (hereinafter referred to as (1) third step). The resulting gel-like product was dried at 110° C. by a vacuum drier and the resulting dry solid was ground to obtain a water absorbent material of the present invention. The evaluation results of characteristics of the resulting water absorbent material are shown in Table 2.

Example 2

In the same operation and manner as in Example 1, except that the amount of acrylic acid was changed to 30 g, the amount of dipentaerythritol hexamethacrylate was changed to 0.1 g, and the amount of sodium hydroxide for neutralization of carboxyl groups originating in acrylic acid was changed to 12.5 g, a water absorbent material of the present invention was obtained. The evaluation results of characteristics of the resulting water absorbent material are shown in Table 2.

Example 3

In a 500 ml four-necked flask equipped with a stirrer, a thermometer, a reflux condenser, a dropping funnel and a nitrogen gas introducing device, 10 g of polysuccinimide obtained in Synthetic Example 2 and 10 g of DMF were charged and dissolved at about 60° C., and then 0.5 g of 2-methacryloyloxyethyl isocyanate was added. As a result, heat was generated. After the reaction was continued for 30 minutes, 125 g of an aqueous solution containing 2.1 g of sodium hydroxide dissolved therein was added and polysuccinimide was hydrolyzed. After the temperature in the system was reduced to about 35° C., 1 g of "ALSTAR B" was charged.

In a 100 ml Erlenmeyer flask, 25 g of acrylic acid, 0.125 g of dipentaerythritol hexamethacrylate and 0.04 g of "THIOKALCOL 20" (laurylmercaptane, manufactured by Kao Corp.) were mixed to prepare an acrylic acid solution. 5 g of this mixed solution was added to the four-necked flask and the rest was transferred to a dropping funnel. After the atmosphere in the system was replaced by a nitrogen gas, 7.5 mg of 2,2-azobisaminodipropane dihydrochloride, 5 mg of ascorbic acid and 57 mg of an aqueous hydrogen peroxide (35%) solution were respectively dissolved in 1 g of ion exchange water. The resulting solutions were added to the above aqueous solution ((1) first step). After 10 minutes, dropwise addition of the acrylic acid solution in the dropping funnel was initiated and was completed over one hour. After one hour has passed since the completion of the reaction, 7.5 g of 2,2-azobisaminodipropane dihydrochloride, 5 mg of ascorbic acid and 57 mg of an aqueous hydrogen peroxide (35%) solution were respectively dissolved again in 1 g of ion exchange water. The resulting solutions were added to the above aqueous solution in this sequence, and then the mixture was heated to about 60° C. and maintained at the same temperature for three hours (hereinafter referred to as (1) second step).

2.4 g of hexamethylenediamine was dissolved in 20 g of ion exchange water and the resulting solution was added to the above aqueous solution, and then the reaction was conducted. Furthermore, 10.4 g of sodium hydroxide was dissolved in 30 g of ion exchange water and the resulting solution was added, thereby to neutralize carboxyl groups originating in acrylic acid ((1) third step). The resulting gel-like product was dried at 110° C. by a vacuum drier and the resulting dry solid was ground to obtain a water absorbent material of the present invention. The evaluation results of characteristics of the resulting water absorbent material are shown in Table 2.

Example 4

In a 500 ml four-necked flask equipped with a stirrer, a thermometer, a reflux condenser, a dropping funnel and a nitrogen gas introducing device, 5 g of polysuccinimide obtained in Synthetic Example 2 and 10 g of DMF were charged and dissolved at about 60° C., and then 0.25 g of 2-methacryloyloxyethyl isocyanate was added. As a result, heat was generated. After the reaction was continued for 30 minutes, the temperature in the system was reduced to about 35° C., 1 g of a pregelatinized starch was charged. After the atmosphere in the four-necked flask was replaced by a nitrogen gas, 7.5 mg of 2,2-azobisaminodipropane dihydrochloride, 5 mg of ascorbic acid and 57 mg of an aqueous hydrogen peroxide (35%) solution were respectively dissolved in 1 g of ion exchange water. The resulting solutions were added to the above aqueous solution, and then the mixture was heated to about 60° C. and maintained for three hours ((1) first step). To the polymer obtained by this step, 25 g of acrylic acid and 25 mg of N,N'-methylenebisacrylamide were added. After the atmosphere in the four-necked flask was replaced by a nitrogen gas, 7.5 g of 2,2-azobisaminodipropane dihydrochloride, 5 mg of ascorbic acid and 57 mg of an aqueous hydrogen peroxide (35%) solution were respectively dissolved again in 1 g of ion exchange water. The resulting solutions were added to the above aqueous solution in this sequence, and then the mixture was heated again to about 60° C. and maintained at the same temperature for three hours ((1) second step). 1.2 g of hexamethylenediamine was dissolved in 20 g of ion exchange water and the resulting solution was added to the above aqueous solution, and then the reaction was conducted. Furthermore, 10.4 g of sodium hydroxide was dissolved in 30 g of ion exchange water and the resulting solution was added, thereby to neutralize carboxyl groups originating in acrylic acid ((1) third step). The resulting gel-like product was dried at 110° C. by a vacuum drier and the resulting dry solid was ground to obtain a water absorbent material of the present invention. The evaluation results of characteristics of the resulting water absorbent material are shown in Table 2.

Comparative Example 1

In a 500 ml four-necked flask equipped with a stirrer, a thermometer, a reflux condenser and a nitrogen gas introducing device, 1 g of a pregelatinized starch, 25 g of acrylic acid, 0.25 g of dipentaerythritol hexamethacrylate and 150 g of ion exchange water were charged. After the atmosphere in the system was replaced by a nitrogen gas, 7.5 mg of 2,2-azobisaminodipropane dihydrochloride, 5 mg of ascorbic acid and 57 mg of an aqueous hydrogen peroxide (35%) solution were respectively dissolved in 1 g of ion exchange water. The resulting solutions were added in this sequence and the reaction was initiated, and then the mixture was maintained at 60° C. for three hours ((1) first step). After the completion of the reaction, 10.4 g of sodium hydroxide was dissolved in 30 g of ion exchange water and the resulting solution was added, thereby to neutralize carboxyl groups originating in acrylic acid ((1) third step). The resulting gel-like product was dried at 110° C. by a vacuum drier and the resulting dry solid was ground. The evaluation results of characteristics of the resulting ground material are shown in Table 2.

Components to be charged of Examples 1 to 4 and Comparative Example 1 are shown in Table 1.

TABLE 1

| | Components to be charged (g) | Example 1 | Example 2 | Example 3 | Example 4 | Comp. Example 1 |
|---|---|---|---|---|---|---|
| | Polysuccinimide (1) | 10 | 10 | — | — | — |
| | Polysuccinimide (2) | — | — | 10 | 5 | — |
| (1) First step | DMF | 20 | 20 | 10 | 10 | — |
| | MCOEI | 0.5 | 0.5 | 0.5 | 0.25 | — |
| | NaOH | 3.3 | 3.3 | 2.1 | — | — |
| | Ion exchange water | 146.7 | 146.7 | 122.9 | — | 150.0 |
| | Pregelatinized starch | 1 | 1 | 1 | 1 | 1 |
| | Acrylic acid | 25 | 30 | 25 | — | 25 |
| | DPMA | 0.25 | 0.1 | 0.125 | — | 0.25 |
| | Laurylmercaptane | — | — | 0.04 | — | — |
| | ABAPHC | 0.0075 | 0.0075 | 0.0075 | 0.0075 | 0.0075 |
| | Ascorbic acid | 0.005 | 0.005 | 0.005 | 0.005 | 0.005 |
| | 35% hydrogen peroxide water | 0.057 | 0.057 | 0.057 | 0.057 | 0.057 |
| | Ion exchange water | 3 | 3 | 3 | 3 | 3 |
| (1) Second step | Acrylic acid | — | — | — | 25 | — |
| | MBAA | — | — | — | 0.025 | — |
| | ABAPHC | — | — | 0.0075 | 0.0075 | — |
| | Ascorbic acid | — | — | 0.005 | 0.005 | — |

TABLE 1-continued

| Components to be charged (g) | | Example 1 | Example 2 | Example 3 | Example 4 | Comp. Example 1 |
|---|---|---|---|---|---|---|
| (1) Third step | 35% hydrogen peroxide water | — | — | 0.057 | 0.057 | — |
| | Ion exchange water | — | — | 3 | 3 | — |
| | Hexamethylenediamine aqueous solution (ion exchange water: 20 g) | 2.4 | 2.4 | 2.4 | 1.2 | — |
| | NaOH aqueous solution (ion exchange water: 30 g) | 10.4 | 12.5 | 10.4 | 10.4 | 10.4 |

Polysuccinimide (1): polysuccinimide (Mw: 20,000) obtained in Synthetic Example 1
Polysuccinimide (2): polysuccinimide (Mw: 3,000) obtained in Synthetic Example 2
MCOEI: 2-methacryloyloxyethyl isocyanate
DPMA: dipentaerythritol hexamethacrylate
ABAPHC: 2,2-azobisaminodipropane dihydrochloride
MBAA: N,N'-methylenebisacrylamide

TABLE 2

| | Water absorption ratio (g/g) | |
|---|---|---|
| | Ion exchange water | 0.9% aqueous solution of sodium chloride |
| Example 1 | 230 | 62 |
| Example 2 | 270 | 70 |
| Example 3 | 237 | 114 |
| Example 4 | 301 | 107 |
| Comparative Example 1 | 400 | 39 |

Example 5

In a 500 ml four-necked flask equipped with a stirrer, a thermometer, a reflux condenser, a dropping funnel and a nitrogen gas introducing device, 121 g of cyclohexane was added, and then 0.9 g of sorbitan monostearate was added thereto and dissolved by heating to 50° C. while stirring. The contents in the flask were cooled to 30° C.

In a 500 ml Erlenmeyer flask, 30 g of acrylic acid was charged and neutralized (75 mol %) by adding dropwise 91.8 g of an aqueous sodium hydroxide solution containing 12.5 g of sodium hydroxide dissolved therein while cooling from outside. To this solution, 21 mg of N,N'-methylenebisacrylamide was added and then 0.104 g of potassium persulfate and 0.0426 g of sodium hypophosphite monohydrate were added and dissolved. The resulting partially neutralized aqueous acrylic acid salt solution containing a polymerization initiator and a crosslinking agent (neutralization degree: 75 mol %) was added in the contents of the above cylindrical round bottom flask and dispersed in the cyclohexane solution containing the surfactant, and then the atmosphere in the system was sufficiently replaced by nitrogen. A bath was heated and the temperature was set to 70° C. and the mixture was maintained at the same temperature for three hours, and then the polymerization reaction was conducted (hereinafter referred to as (2) first step). The polymer-containing slurry solution obtained by this step was cooled to 20° C.

In a separate 500 ml four-necked flask equipped with a stirrer, a thermometer, a reflux condenser, and a nitrogen gas introducing device, 7 g of polysuccinimide obtained in Synthetic Example 2 and 10 g of DMF were charged and dissolved at about 60° C., and then 0.35 g of 2-methacryloyloxyethyl isocyanate was added. As a result, heat was generated. After the reaction was continued for 30 minutes, 10 g of an aqueous sodium hydroxide solution containing 1.44 g of sodium hydroxide dissolved therein was added, thereby hydrolyzing polysuccinimide (hereinafter referred to as (2) second step). In the same manner as described above, 20.3 g of an aqueous partially neutralized sodium acrylate solution (neutralization degree: 75 mol %) was prepared from 5 g of the aqueous acrylic acid solution and then added to the above solution. Furthermore, 1.73 g of potassium persulfate, 21 mg of N,N'-methylenebisacrylamide and 7.1 mg of sodium hypophosphite monohydrate were added and dissolved. The aqueous monomer solution thus obtained was transferred to the dropping funnel and then slowly added dropwise to the polymer slurry solution maintained at 20° C. over 30 minutes. After the atmosphere in the flask was sufficiently replaced by nitrogen, the contents were heated to 70° C. and maintained at the same temperature for three hours, and furthermore, the polymerization reaction was conducted (hereinafter referred to as (2) third step). Under reduced pressure, cyclohexane and water were removed. The evaluation results of characteristics of the resulting water absorbent material as gel-like particles are shown in Table 4.

Comparative Example 2

In a 500 ml four-necked flask equipped with a stirrer, a thermometer, a reflux condenser, a dropping funnel, and a nitrogen gas introducing device, 121 g of cyclohexane was added, and then 0.9 g of sorbitan monostearate was added thereto and dissolved by heating to 50° C. while stirring. The contents in the flask were cooled to 30° C. In a 500 ml Erlenmeyer flask, 30 g of acrylic acid was charged and neutralized (75 mol %) by adding dropwise 91.8 g of an aqueous sodium hydroxide solution containing 12.5 g of sodium hydroxide dissolved therein while cooling from outside. To this solution, 21 mg of N,N'-methylenebisacrylamide was added and then 0.104 g of potassium persulfate and 0.0426 g of sodium hypophosphite monohydrate were added and dissolved. The resulting partially neutralized aqueous acrylic acid salt solution containing a polymerization initiator and a crosslinking agent (neutralization degree: 75 mol %) was added in the contents of the above cylindrical round bottom flask and dispersed in the cyclohexane solution containing the surfactant, and then the atmosphere in the system was sufficiently replaced by nitrogen. A bath was heated and the temperature was set to 70° C. and the mixture was maintained at the same temperature for three hours, and then the polymerization reaction was conducted (hereinafter referred to as (2) first step).

In the same manner as described above, 20.3 g of an aqueous partially neutralized sodium acrylate solution (neutralization degree: 75 mol %) was prepared from 5 g of the aqueous acrylic acid solution in a 100 ml Erlenmeyer flask and was then added. Furthermore, 1.73 mg of potassium persulfate, 21 mg of N,N'-methylenebisacrylamide and 7.1 mg of sodium hypophosphite monohydrate were added and dissolved. The aqueous monomer solution thus obtained was transferred to the dropping funnel and then slowly added dropwise to the polymer slurry solution maintained at 20° C. over 30 minutes. After the atmosphere in the flask was sufficiently replaced by nitrogen, the contents were heated to 70° C. and maintained at the same temperature for three hours, and furthermore, the polymerization reaction was conducted ((2) third step). Under reduced pressure, cyclohexane and water were removed. The evaluation results of characteristics of the resulting water absorbent material as gel-like particles are shown in Table 4.

Components to be charged of Example 5 and Comparative Example 2 are shown in Table 3.

g of sodium hydroxide dissolved therein was added and then 50 g of a powder of polysuccinimide obtained in Synthetic Example 2 was added to prepare an aqueous solution of polysuccinimide. After the temperature was raised to 90° C., 5.0 g of glycidyl methacrylate was added and the reaction was conducted for one hour to obtain an aqueous solution containing a hydrolysate of polysuccinimide having methacryloyl groups introduced therein.

In a 100 ml Erlenmeyer flask, 0.75 g of "DK ESTER F-160" [sucrose fatty acid ester (HLB=16), manufactured by DAI-ICHI KOGYO SEIYAKU CO., LTD.] was weighed and dissolved by adding 29 g of cyclohexane and heating to 50° C. The resulting solution was added to 7.7 g of the aqueous solution obtained by the above operation, followed by stirring to obtain a dispersion of polysuccinimide having methacryloyl groups introduced therein in an aqueous hydrolyzed solution (hereinafter referred to as (3) first step).

In a separate 500 ml four-necked flask equipped with a stirrer, a thermometer, a reflux condenser, and a nitrogen gas introducing device, 164 g of cyclohexane was added, and then 0.75 g of "DK ESTER F-90" was added and dissolved by heating to 50° C. with stirring. The contents in the flask were cooled to 30° C. In a 500 ml Erlenmeyer flask, 18.4 g of sodium sulfoethylmethacrylate was added. To this solution, 18.4 g of acrylamide and 3.9 mg of N,N'-methylenebisacrylamide were added and, furthermore, 0.05 g of ammonium persulfate was added and dissolved. The resulting aqueous solution containing a polymerization ini-

TABLE 3

| | Components to be charged (g) | Example 5 | Comp. Example 2 |
|---|---|---|---|
| (2) First step | Cyclohexane | 121 | 121 |
| | Sorbitan monostearate | 0.9 | 0.9 |
| | Acrylic acid | 30 | 30 |
| | NaOH | 12.5 | 12.5 |
| | Ion exchange water | 79.3 | 79.3 |
| | MBAA | 0.021 | 0.021 |
| | Potassium persulfate | 0.104 | 0.104 |
| | Sodium hypophosphite monohydrate | 0.0426 | 0.0426 |
| (2) Second step | Polysuccinimide (2) | 7 | — |
| | DMF | 10 | — |
| | MCOEI | 0.35 | — |
| | NaOH | 1.44 | — |
| | Ion exchange water | 8.56 | — |
| (2) Third step | 75 mol % partially neutralized sodium acrylate | 20.3 | 20.3 |
| | Potassium persulfate | 0.00173 | 0.00173 |
| | MBAA | 0.021 | 0.021 |
| | Sodium hypophosphite monohydrate | 0.0071 | 0.0071 |

MBAA: N,N'-methylenebisacrylamide
Polysuccinimide (2): polysuccinimide (Mw: 3,000) obtained in Synthetic Example 2
MCOEI: 2-methacryloyloxyethyl isocyanate

TABLE 4

| | Water absorption ratio (g/g) | |
|---|---|---|
| | Ion exchange water | 0.9% aqueous solution of sodium chloride |
| Example 5 | 615 | 135 |
| Comp. Example 2 | 676 | 67 |

Example 6

In a 500 ml four-necked flask equipped with a stirrer, a thermometer, a reflux condenser and a nitrogen gas introducing device, 75 g of an aqueous solution containing 20.6 tiator and a crosslinking agent, which is essentially composed of sodium sulfoethylmethacrylate and acrylamide as a main component, was added to the contents in a cylindrical round bottom flask and was dispersed in a siloxane solution containing a surfactant at a stirring rate of 300 rpm and, at the same time, the atmosphere in the system was sufficiently replaced by nitrogen. Then, the polymerization reaction was initiated by heating. After a while, heat was generated. After five minutes had passed since the peak of heat generation, the resulting dispersion of a hydrolysate of polysuccinimide having methacryloyl groups introduced therein in an aqueous solution was added at a time. The mixture was maintained at 60 to 65° C. for three hours. After the completion of the reaction, the four-necked flask was equipped with a water dispenser and azeotropic dehydration was conducted by raising the temperature in the system to 70 to 80° C. After azeotropic dehydration was conducted until the amount of water in the system became 35% based on the solid content to be charged, the temperature in the system was cooled to about 40° C. and a cyclohexane phase was separated by decantation. Subsequently, water was removed from a wet polymer by vacuum drying to obtain a water absorbent material as gel-like particles (hereinafter referred to as (3) second step). The evaluation results of this water absorbent material are shown in Table 6.

Comparative Example 3

In a 500 ml four-necked flask equipped with a stirrer, a thermometer, a reflux condenser, and a nitrogen gas introducing device, 164 g of cyclohexane was added, and then 0.75 g of "DK ESTER F-90" was added and dissolved by heating to 50° C. with stirring. The contents in the flask were cooled to 30° C. In a 500 ml Erlenmeyer flask, 18.4 g of sodium sulfoethylmethacrylate was added. To this solution, 18.4 g of acrylamide and 3.9 mg of N,N'-methylenebisacrylamide were added, and furthermore, 0.05 g of ammonium persulfate was added and dissolved. The resulting aqueous solution containing a polymerization initiator and a crosslinking agent, which is essentially composed of sodium sulfoethylmethacrylate and acrylamide as a main component, was added to the contents in a cylindrical round bottom flask and was dispersed in a siloxane solution containing a surfactant at a stirring rate of 300 rpm, and at the same time, the atmosphere in the system was sufficiently replaced by nitrogen. Then, the polymerization reaction was initiated by heating. The mixture was maintained at 60 to 65° C. for three hours. After the completion of the reaction, the four-necked flask was equipped with a water dispenser and azeotropic dehydration was conducted by raising the temperature in the system to 70 to 80° C. After azeotropic dehydration was conducted until the amount of water in the system became 35% based on the solid content to be charged, the temperature in the system was cooled to about 40° C. and a cyclohexane phase was separated by decantation. Subsequently, water was removed from a wet polymer by vacuum drying to obtain a water absorbent material as gel-like particles (hereinafter referred to as (3) third step). The evaluation results of this water absorbent material are shown in Table 6.

Example 7

In a 500 ml Erlenmeyer flask, 16.5 g of 2-acrylamide-2-methylpropanesulfonic acid was charged and neutralized (60 mol %) by adding dropwise 78.4 g of an aqueous sodium hydroxide solution containing 1.9 g of sodium hydroxide dissolved therein while cooling from outside. To this solution, 14.7 g of acrylamide and 23.1 mg of N,N'-methylenebisacrylamide were added and then 0.05 g of ammonium persulfate was added and dissolved. The same operation was conducted, except that the resulting aqueous solution containing a polymerization initiator and a crosslinking agent, which is essentially composed of 2-acrylamide-2-methylpropanesulfonic acid, a sodium salt thereof and acrylamide as a main component was used, a water absorbent material of the present invention as gel-like particles was obtained. The evaluation results of characteristics of the water absorbent material are shown in Table 6.

Example 8

In a 500 ml Erlenmeyer flask, 30 g of polymer particles obtained in Example 7 were weighed, and then a mixed solution of 1.2 g of acetone, 2.1 g of ion exchange water, 0.09 g of glycidyl methacrylate and 0.09 g of ammonium persulfate as well as 0.3 g of "200CF" [hydrophilic silica, manufactured by Nippon Aerosil Co., Ltd.] were uniformly dispersed, together with the polymer particles. The surface crosslinking treatment of the polymer was conducted by vacuum-drying the wet polymer at 108° C. for one hour (hereinafter referred to as (3) third step). The evaluation results of the resulting water absorbent material are shown in Table 6.

Comparative Example 4

The same operation as in Example 7 was conducted to prepare an aqueous solution containing a polymerization initiator and a crosslinking agent, which is essentially composed of 2-acrylamide-2-methylpropanesulfonic acid, a sodium salt thereof and acrylamide as a main component, was prepared. The same operation as in Comparative Example 3 was conducted to obtain a water absorbent material of the present invention as gel-like particles. The evaluation results of the resulting water absorbent material are shown in Table 6.

Comparative Example 5

4.44 g of polyethylene glycol diacrylate was dissolved in 5500 g of an aqueous solution of sodium acrylate (neutralization ratio: 75 mol %), and after deaerating with a nitrogen gas, 2.4 g of sodium persulfate and 0.12 g of 1-ascorbic acid were added and the polymerization was conducted. After the completion of the polymerization, the resulting hydrous gel-like particles were further ground and dried in a hot-air dryer at 150° C. so that the water content of the hydrous gel-like particles became 5% or less. The dried substance was granulated by a roll granulater and then passed through an ASTM 20 mesh metal wire to obtain a water absorbent polymer in an amorphous ground form.

100 parts of this water absorbent polymer was mixed with an aqueous solution of 1 part of sodium polyaspartate (molecular weight: 10000) and 5 parts of water to obtain an absorber composition. The evaluation results of characteristics of this water absorbent material are shown in Table 6.

Components to be charged of Examples 6 to 8 and Comparative Examples 3 and 4 are shown in Table 5.

TABLE 5

| Components to be charged (g) | | Example 6 | Example 7 | Example 8 | Comp. Example 3 | Comp. Example 4 |
|---|---|---|---|---|---|---|
| (3) First step | Polysuccinimide (2) | 3 | 3 | 3 | — | — |
| | GMA | 0.3 | 0.3 | 0.3 | — | — |
| | NaOH | 1.2 | 1.2 | 1.2 | — | — |
| | Ion exchange water | 3.2 | 3.2 | 3.2 | — | — |
| | Sucrose ester F-160 (HLB = 16) | 0.75 | 0.75 | 0.75 | — | — |
| | Cyclohexane | 20 | 20 | 20 | — | 20 |
| (3) Second step | Sucrose ester F-90 (HLB = 9) | 0.75 | 0.75 | 0.75 | — | — |
| | Cyclohexane | 164 | 164 | 164 | — | — |
| | Na sulfomethyl methacrylate | 18.4 | — | — | 18.4 | — |
| | AMPS | — | 16.5 | 16.5 | 16.5 | — |
| | Acrylamide | 18.4 | 18.4 | 18.4 | 18.4 | 18.4 |
| | NaOH | — | 1.9 | 1.9 | — | 8.3 |
| | Ion exchange water | 80.9 | 76.5 | 76.5 | 80.9 | 76.5 |
| | MBAA | 0.0039 | 0.0039 | 0.0039 | 0.0039 | 0.0039 |
| | APS | 0.05 | 0.05 | 0.05 | 0.05 | 0.05 |
| (3) Third step | GMA | — | — | 0.09 | — | — |
| | APS | — | — | 0.09 | — | — |
| | Ion exchange water | — | — | 2.1 | — | — |
| | Acetone | — | — | 1.2 | — | — |
| | Hydrophilic silica 200CF | — | — | 0.3 | — | — |

GMA: glycidyl methacrylate
AMPS: 2-acrylamide-2-methylpropanesulfonic acid
MBAA: N,N'-methylenebisacrylamide
APS: ammonium persulfate
Polysuccinimide (2): polysuccinimide (Mw: 3,000) obtained in Synthetic Example 2

TABLE 6

| | Water absorption ratio (g/g) | | | | |
|---|---|---|---|---|---|
| | Ion exchange water | 0.9% aqueous solution of NaCl | Artificial seawater | Water absorption rate (seconds) | Gel strength (g/cm$^2$) |
| Example 6 | 715 | 121 | 55 | 120 | 2.4 |
| Example 7 | 520 | 49 | 30 | 64 | 6.0 |
| Example 8 | 490 | 45 | 28 | 55 | 12.0 |
| Comp. Example 3 | 587 | 98 | 47 | 195 | 2.4 |
| Comp. Example 4 | 440 | 41 | 27 | 95 | 6.0 |
| Comp. Example 5 | 380 | 37 | 3 | 257 | 1.2 |

As is apparent from Table 6, the water absorbent materials of the present invention have high water absorption ratio and high water absorption rate in ion exchange water, an aqueous 0.9% NaCl solution, and artificial seawater as compared with the water absorbent materials of Comparative Examples and water absorption performances are improved.

INDUSTRIAL APPLICABILITY

The water absorbent material of the present invention has high water absorption properties for high concentration salt-containing solutions such as seawater, aqueous deliquescent calcium chloride solution, blood, and body fluids (e.g. urine, sweat, etc.) as compared with a conventional water absorbent material by using a copolymer containing polysaccharides as a copolymer component, and can improve water absorption properties to salt-containing solutions without impairing a water absorption ratio and a water absorption rate by using a monomer having a sulfonic acid group containing ethylenically unsaturated double bond. Therefore, the water absorbent material of the present invention can be widely used as water absorbent materials for water sealing materials, civil engineering materials, materials for agricultural/horticultural disposable sanitary materials, and household articles.

The absorbent article of the present invention is suited for use in disposable diapers for infants, adults, and persons suffering from incontinence, and in sanitary napkins because of its excellent absorbency of urine and body fluids as well as excellent urine leakage inhibition effects.

What is claimed is:

1. A water absorbent material comprising a copolymer of an anhydropolyamino acid having at least one ethylenically unsaturated double bond in a molecule (A) and a water-soluble monomer having an ethylenically unsaturated double bond (B).

2. A water absorbent material according to claim 1, wherein the water-soluble monomer having an ethylenically unsaturated double bond (B) is at least one selected from the group consisting of (meth)acrylic acid, alkali metal salt of (meth)acrylic acid, ammonium salt of (meth)acrylic acid, and an amidated compound of (meth)acrylic acid.

3. A water absorbent material according to claim 1, wherein the water-soluble monomer having an ethylenically unsaturated double bond (B) is a monomer having an ethylenically unsaturated double bond, and a sulfonic acid group and/or a sulfonate group in a molecule.

4. A water absorbent material according to claim 1, wherein the anhydropolyamino acid having at least one ethylenically unsaturated double bond in a molecule (A) is a reaction product of an anhydropolyamino acid having no ethylenically unsaturated double bond in a molecule (A-1) and a compound which has an ethylenically unsaturated double bond and a functional group having reactivity with the anhydropolyamino acid (A-1) in a molecule (A-2).

5. A water absorbent material according to claim 1, wherein the copolymer comprises gel particles.

6. A water absorbent material according to claim 4, wherein the compound which has an ethylenically unsaturated double bond and a functional group having reactivity with the anhydropolyamino acid (A-1) in a molecule (A-2) is a compound represented by the following general formula [I]:

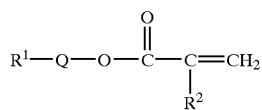

wherein $R^1$ represents at least one functional group selected from the group consisting of amino group, epoxy group, carboxyl group, carbodimide group, oxazoline group, imino group and isocyanate group, Q represents an alkylene group having 1 to 10 carbon atoms, and $R^2$ represents hydrogen or an alkylene group having 1 to 4 carbon atoms.

7. A water absorbent material according to claim 4, wherein the anhydropolyamino acid having no ethylenically unsaturated double bond in a molecule (A-1) is polysuccinimide.

8. A water absorbent material according to claim 1, wherein a portion or all of the anhydropolyamino acid having an ethylenically unsaturated double bond in a molecule (A) is hydrolyzed.

9. A water absorbent material according to claim 1, wherein a water absorption ratio of a physiological saline solution is 10 g/g or more.

10. An absorbent article comprising an absorber comprising a water absorbent material and a fiber material arranged between a liquid-permeable sheet and a liquid-impermeable sheet, wherein the water absorbent material is a water absorbent material comprising a copolymer of an anhydropolyamino acid having at least one ethylenically unsaturated double bond in a molecule (A) and a water-soluble monomer having an ethylenically unsaturated double bond (B).

11. An absorbent article according to claim 10, wherein the copolymer comprises gel particles.

* * * * *